US012262714B2

(12) United States Patent
Yun et al.

(10) Patent No.: US 12,262,714 B2
(45) Date of Patent: Apr. 1, 2025

(54) SUPERABSORBENT POLYMER AND PREPARATION METHOD THEREOF

(71) Applicant: LG Chem, Ltd., Seoul (KR)

(72) Inventors: Haesung Yun, Daejeon (KR); Hyungsam Choi, Daejeon (KR); Dong Hyun Kim, Daejeon (KR); Seonjung Jung, Daejeon (KR); Ji Seok Lee, Daejeon (KR); Jin Woo Lee, Daejeon (KR); Jun Kyu Kim, Daejeon (KR); Byungguk Kim, Daejeon (KR); Sanggon Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 512 days.

(21) Appl. No.: 17/774,202

(22) PCT Filed: Nov. 13, 2020

(86) PCT No.: PCT/KR2020/015821
§ 371 (c)(1),
(2) Date: May 4, 2022

(87) PCT Pub. No.: WO2021/096230
PCT Pub. Date: May 20, 2021

(65) Prior Publication Data
US 2022/0346379 A1    Nov. 3, 2022

(30) Foreign Application Priority Data

Nov. 13, 2019 (KR) .................. 10-2019-0145146
May 7, 2020 (KR) .................. 10-2020-0054684
Nov. 12, 2020 (KR) .................. 10-2020-0151154

(51) Int. Cl.
| | | |
|---|---|---|
| C08F 220/60 | (2006.01) | |
| A01N 47/44 | (2006.01) | |
| A01P 1/00 | (2006.01) | |
| A61L 15/24 | (2006.01) | |
| A61L 15/46 | (2006.01) | |
| A61L 15/60 | (2006.01) | |
| C08F 220/06 | (2006.01) | |
| C08J 3/24 | (2006.01) | |

(52) U.S. Cl.
CPC .......... A01N 47/44 (2013.01); A01P 1/00 (2021.08); A61L 15/24 (2013.01); A61L 15/46 (2013.01); A61L 15/60 (2013.01); C08F 220/06 (2013.01); C08J 3/245 (2013.01); A61L 2300/404 (2013.01); C08J 2333/02 (2013.01)

(58) Field of Classification Search
CPC ..... B01J 20/261; C08F 220/60; C08F 220/06; A01N 47/44
See application file for complete search history.

(56) References Cited

U.S. PATENT DOCUMENTS

| | | | |
|---|---|---|---|
| 5,981,668 A | 11/1999 | Fujita et al. | |
| 6,087,448 A | 7/2000 | Mitchell et al. | |
| 2003/0113291 A1 | 6/2003 | Schmidt et al. | |
| 2005/0171235 A1 | 8/2005 | Harren et al. | |
| 2016/0368761 A1 | 12/2016 | Geiger et al. | |
| 2019/0046682 A1 | 2/2019 | Choi et al. | |
| 2019/0351391 A1 | 11/2019 | Lee et al. | |
| 2020/0122117 A1* | 4/2020 | Lee .................. A61L 15/46 | |
| 2020/0123281 A1 | 4/2020 | Kim et al. | |
| 2020/0325109 A1 | 10/2020 | Zhang et al. | |
| 2021/0087337 A1 | 3/2021 | Ghosh et al. | |

FOREIGN PATENT DOCUMENTS

| | | | |
|---|---|---|---|
| CN | 1296397 C | | 1/2007 |
| CN | 101210062 A | | 7/2008 |
| CN | 105037645 A | | 11/2015 |
| CN | 106832347 | * | 6/2017 |
| CN | 106832347 A | | 6/2017 |
| CN | 108239215 | * | 7/2018 |
| CN | 108239215 A | | 7/2018 |
| CN | 108774759 A | | 11/2018 |
| CN | 108884236 A | | 11/2018 |
| CN | 106832347 B | | 3/2019 |
| CN | 109715709 A | | 5/2019 |
| CN | 110067042 A | | 7/2019 |
| CN | 110198976 A | | 9/2019 |
| EP | 0839841 A2 | | 5/1998 |
| EP | 3456760 A1 | | 3/2019 |
| EP | 3564297 A1 | | 11/2019 |
| EP | 3998295 A1 | | 5/2022 |
| JP | H01144408 A | | 6/1989 |
| JP | H06166726 A | | 6/1994 |
| JP | H09248454 A | | 9/1997 |
| JP | H11044408 A | | 2/1999 |
| JP | 2000007505 A | | 1/2000 |
| JP | 2000319337 A | | 11/2000 |
| JP | 2001039802 A | | 2/2001 |

(Continued)

OTHER PUBLICATIONS

Translation of CN106832347 (Year: 2017).*
Translation of CN 108239215 (Year: 2018).*
Schwalm, Reinhold, "UV Coatings Basics, Recent Developments and New Application", Elsevier Science, 2007 (Dec. 21, 2006). p. 115.
Weiss, Philip. Principles of polymerization, 2nd ed., George Odian, Wiley-Interscience, New York, 1981, (Oct. 1981) p. 203.
Forsgren-Brusk, Ulla et al. "Method for Bacterial Growth and Ammonia Production and Effect of Inhibitory Substances In Disposable Absorbent Hygiene Products." Journal of Wound, Ostomy and Continence Nursing 44 (Jan./Feb. 2017): pp. 78-83.

(Continued)

*Primary Examiner* — Robert C Boyle
(74) *Attorney, Agent, or Firm* — Lerner David LLP

(57) ABSTRACT

Provided are both a superabsorbent polymer capable of continuously and safely exhibiting an improved bacterial growth inhibitory property and a deodorant property without deterioration in the physical properties of the superabsorbent polymer, such as water retention capacity, absorption under pressure, etc., as well as a preparation method for the superabsorbent polymer.

11 Claims, 4 Drawing Sheets

(56) References Cited

FOREIGN PATENT DOCUMENTS

| | | | |
|---|---|---|---|
| JP | 2001523740 A | | 11/2001 |
| JP | 2003-055108 A | | 2/2003 |
| JP | 3625304 B2 | | 3/2005 |
| JP | 2005532422 A | | 10/2005 |
| JP | 2006524537 A | | 11/2006 |
| JP | 2007327008 A | | 12/2007 |
| JP | 4036954 B2 | | 1/2008 |
| JP | 4261636 B2 | | 4/2009 |
| JP | 5167306 B2 | | 3/2013 |
| JP | 2019518838 A | | 7/2019 |
| JP | 2019528309 A | | 10/2019 |
| JP | 2021-512967 A | | 5/2021 |
| KR | 20020091274 A | | 12/2002 |
| KR | 20160111504 A | | 9/2016 |
| KR | 101797391 B1 | | 11/2017 |
| KR | 20190035313 A | | 4/2019 |
| KR | 20190060588 A | | 6/2019 |
| KR | 20190061391 A | | 6/2019 |
| KR | 20190135038 A | | 12/2019 |
| RU | 2378290 | * | 1/2010 |
| RU | 2669563 C2 | | 10/2018 |
| WO | 2004080499 A1 | | 9/2004 |
| WO | 2015014825 A1 | | 2/2015 |
| WO | WO 2019/103317 | * | 5/2019 |

OTHER PUBLICATIONS

International Search Report for PCT/KR2020/015821 dated Feb. 26, 2021. 3 pgs.

Xue, Y. et al., "Antimicrobial Polymeric Materials with Quaternary Ammonium and Phosphonium Salts," International Journal of Molecular Sciences, Feb. 6, 2015, vol. 16, No. 2, pp. 3626-3655.

Liu, X. et al., "Modified acrylic-based superabsorbents with hydrophobic monomers: synthesis, characterization and swelling behaviors," Journal of Polymer Research, Aug. 21, 2010, vol. 18, No. 5, pp. 897-905.

Li, X. et al. "Synthesis and Water Absorbency of Polyampholytic Hydrogels with Antibacterial Activity," Journal of applied polymer science, Jan. 2, 2009, vol. 112, No. 1, pp. 439-446.

International Search Report for Application No. PCT/KR2021/013807 mailed Jan. 25, 2022, pp. 1-3.

Buchholz, F.L. et al., "Modern Superabsorbent Polymer Technology," Chapter 3, pp. 69-78, Copyright © 1998 by John Wiley & Son.

Schwalm, R. "UV Coatings: Basics, Recent Developments and New Applications," Dec. 2006, p. 115, Elsevier.

Odian, G. "Principles of Polymerization" Dec. 1981, p. 203, John Wiley & Sons, Inc.

Search Report dated May 7, 2024 from the Office Action for Chinese Application No. 202180068970.3 issued May 9, 2024, 2 pages.

Zhang, Y. et al., "Synthesis and Antimicrobial Activity of Some Cross-linked Copolymers with Alkyl Chains of Various Lengths," Journal of Applied Polymer Science, Dec. 1, 2010, vol. 120, 1767-1773 (2011).

Extended European Search Report including Written Opinion for Application No. 21878027.8 dated Feb. 5, 2024, pp. 1-9.

Search Report dated Jan. 31, 2023 from the Office Action for Chinese Application No. 202080074044.2 issued Feb. 6, 2023, 3 pages. [See p. 1-2, categorizing the cited references].

Database Caplus [Online] Chemical Abstracts Service; Jan. 1, 2008 (Jan. 1, 2008), Pekar, S.S. et al., "Study of biocidal and toxicological characteristics of new polyacrylamide flocculants," 1 Page. XP055968731.

Extended European Search Report including Written Opinion for Application No. 20886497.5 dated Oct. 25, 2022, pp. 1-7.

Gerasin, V.A. et al., "Guanidine-Containing Organomineral Complexes as Biocide Additives to Polymeric Composites," Russian Journal of Applied Chemistry, Nov. 8, 2018 (Nov. 8, 2018), pp. 1297-1304, vol. 91, No. 8, Pleiades Publishing, Moscow. XP036630655.

Menyashev, M.R. et al., "Guanidine methacrylate and methacryloyl guanidine hydrochloride: Synthesis and polymerization," Polymer Science. Series B, Oct. 20, 2016 (Oct. 10, 2016), pp. 556-563, vol. 58, No. 5. XP055672566.

Zhang, H. et al., "Synthesis of novel guanidine-based ABA triblock copolymers and their antimicrobial honeycomb films," Polymer Chemistry, Jun. 26, 2018 (Jun. 26, 2018), pp. 3922-3930, vol. 9, No. 28. XP055872062.

\* cited by examiner

[FIG. 1]
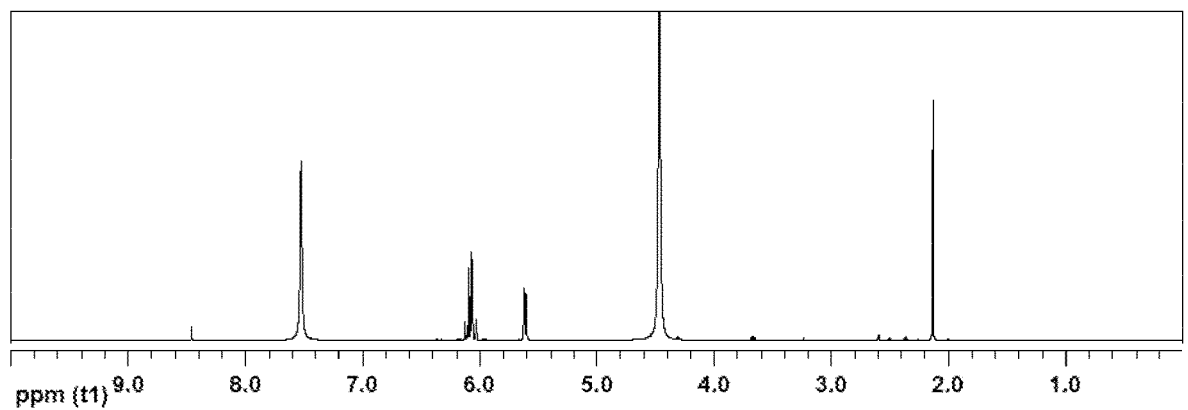

[FIG. 2]
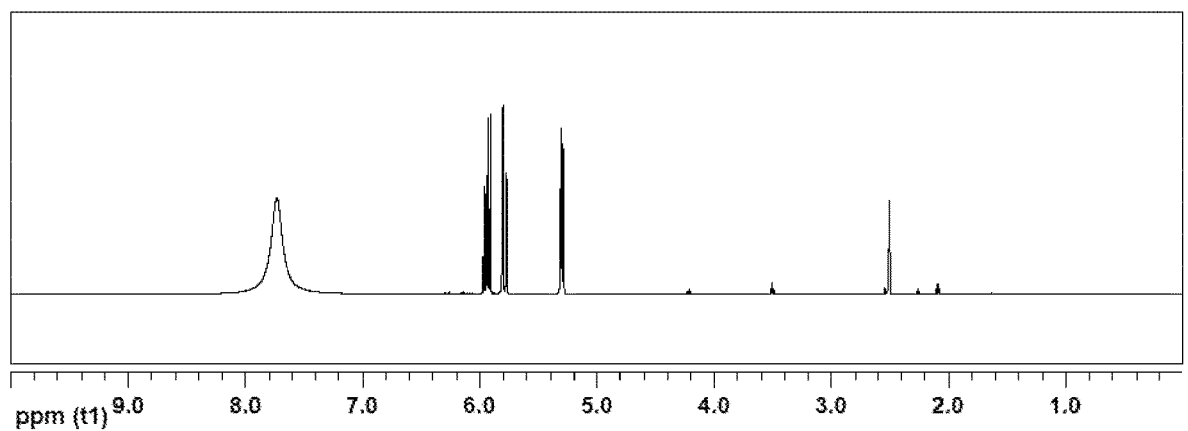

[FIG. 3]
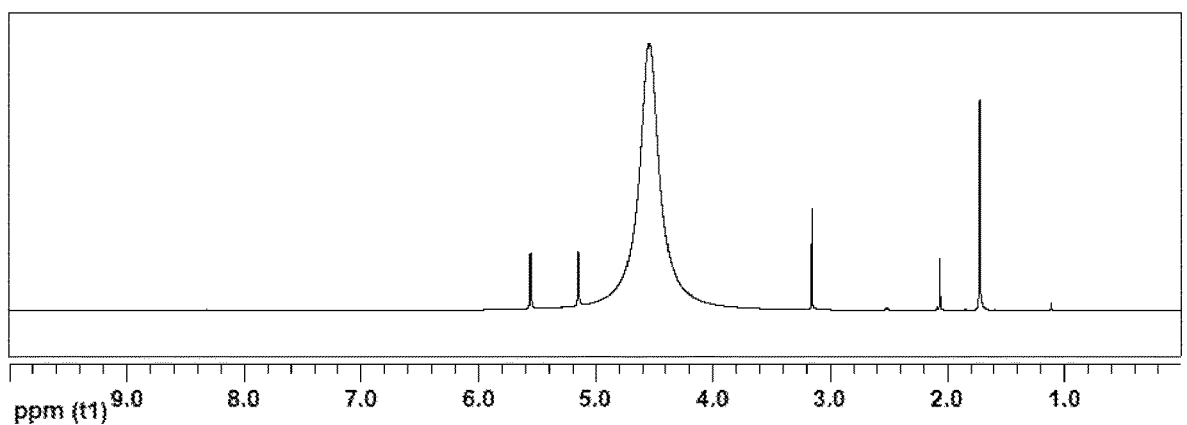

[FIG. 4]
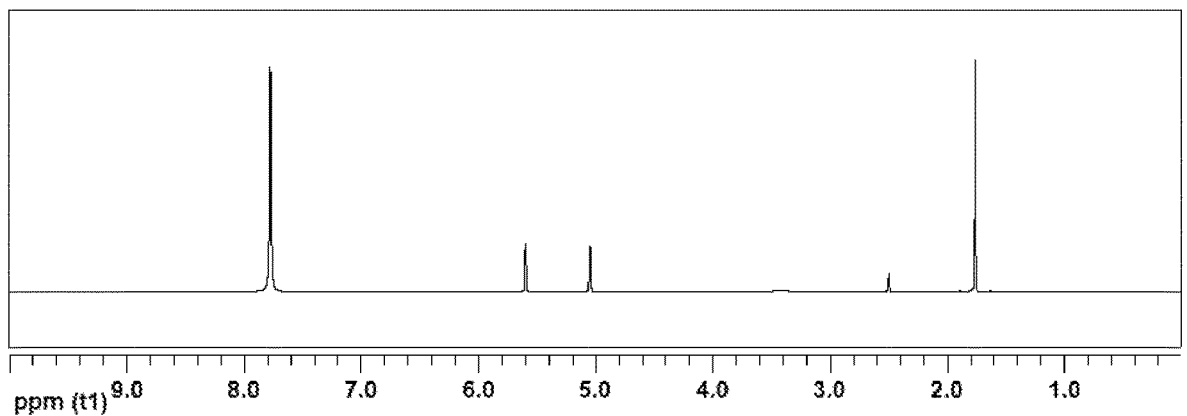

SUPERABSORBENT POLYMER AND PREPARATION METHOD THEREOF

CROSS-REFERENCE TO RELATED APPLICATION(S)

This application is a national phase entry under 35 U.S.C. § 371 of International Application No. PCT/KR2020/015821, filed on Nov. 13, 2020, which claims priority to Korean Patent Application No. 10-2019-0145146, filed on Nov. 13, 2019, Korean Patent Application No. 10-2020-0054684, filed on May 7, 2020 and Korean Patent Application No. 10-2020-0151154, filed on Nov. 12, 2020, the disclosures of which are hereby incorporated by reference herein in their entirety.

TECHNICAL FIELD

The present technology relates to a superabsorbent polymer capable of continuously and safely exhibiting improved bacterial growth inhibitory property and deodorant property while exhibiting excellent water retention capacity and absorption under pressure, and a preparation method thereof.

TECHNICAL FIELD

Cross-Reference to Related Application(s)

The present application is based on, and claims priority from, Korean Patent Application Nos. 10-2019-0145146, 10-2020-0054684, and 10-2020-0151154, filed on Nov. 13, 2019, May 7, 2020, and Nov. 12, 2020, respectively, the disclosures of which are hereby incorporated by reference herein in their entirety.

The present technology relates to a superabsorbent polymer capable of continuously and safely exhibiting improved bacterial growth inhibitory property and deodorant property while exhibiting excellent water retention capacity and absorption under pressure, and a preparation method thereof.

BACKGROUND ART

A superabsorbent polymer (SAP) is a synthetic polymeric material capable of absorbing moisture from 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, etc., but also for water retaining soil products for gardening, water stop materials for the civil engineering and construction, sheets for raising seedling, fresh-keeping agents for food distribution fields, materials for poultice, electrical insulation applications or the like.

In particular, superabsorbent polymers are most widely applied to hygienic goods or disposable absorption products, such as disposable diapers for children or diapers for adults. Among them, when superabsorbent polymers are applied to adult diapers, secondary odor caused by bacterial growth generates a problem of significantly giving consumers an unpleasant feeling. In order to solve this problem, there have been attempts to introduce various bacterial growth inhibitory components or deodorizing or antimicrobial functional components into superabsorbent polymers, etc.

However, in the existing attempts to introduce an antimicrobial agent inhibiting bacterial growth into superabsorbent polymers, it is not easy to select and introduce antimicrobial agent components which do not deteriorate basic physical properties of the superabsorbent polymer while exhibiting excellent bacterial growth inhibitory property and deodorant property, being harmless to the human body, and satisfying economic efficiency.

For example, there has been an attempt to introduce antimicrobial agent components containing antimicrobial metal ions such as silver, copper, zinc, e.g., copper oxide, etc., into superabsorbent polymers. These antimicrobial metal ion-containing components may impart deodorant property by destroying the cell walls of microorganisms such as bacteria, etc., and killing bacteria with enzymes that may cause odor in the superabsorbent polymers. However, the metal ion-containing components are classified as a BIOCIDE material that kills even microorganisms beneficial to the human body. For this reason, when the superabsorbent polymer is applied to hygiene products such as diapers for children or adults, etc., the introduction of the antimicrobial agent components containing metal ions is excluded as much as possible.

Meanwhile, when an antimicrobial agent inhibiting bacterial growth is introduced into superabsorbent polymers, a method of blending the superabsorbent polymers with a small amount of the antimicrobial agent has been mainly employed. However, when this blending method is employed, it is practically difficult to uniformly maintain the bacterial growth inhibitory property over time. Moreover, such a blending method may cause non-uniform applicability and desorption of the antimicrobial agent component during the process of blending the superabsorbent polymer with the antimicrobial agent, and there is also a disadvantage in that it is necessary to install a new facility for the blending.

Accordingly, there is a continuous demand for the development of a technology related to superabsorbent polymers capable of exhibiting excellent bacterial growth inhibitory property and deodorant property without deterioration in basic physical properties of the superabsorbent polymers.

DETAILED DESCRIPTION OF THE INVENTION

Technical Problem

Accordingly, there is provided a superabsorbent polymer capable of continuously and safely exhibiting excellent bacterial growth inhibitory property and deodorant property while maintaining excellent basic physical properties of the superabsorbent polymer, such as water retention capacity, absorption under pressure, etc., and a preparation method thereof.

There is also provided a hygiene product uniformly exhibiting excellent bacterial growth inhibitory property and deodorant property for a long time and also maintaining excellent basic absorption properties by comprising the superabsorbent polymer.

Technical Solution

According to one embodiment of the present invention, there is provided a superabsorbent polymer comprising:
  a base polymer powder comprising a crosslinked polymer of water-soluble ethylene-based unsaturated monomers having acidic groups of which at least a part are neutralized, and a polymerizable antimicrobial monomer; and a surface crosslinked layer formed on the base polymer powder, in which the crosslinked polymer is additionally crosslinked by a surface crosslinking agent;

wherein the polymerizable antimicrobial monomer comprises one or more of guanidine acrylate and salts thereof.

According to another embodiment of the present invention, there is provided a method of preparing the superabsorbent polymer, the method comprising the steps of:

carrying out a crosslinking polymerization of water-soluble ethylene-based unsaturated monomers having acidic groups of which at least a part are neutralized, and a polymerizable antimicrobial monomer, in the presence of an internal crosslinking agent, to form a hydrogel polymer;

drying, pulverizing, and classifying the hydrogel polymer to form a base polymer powder; and carrying out additional crosslinking of the base polymer powder by heat treatment in the presence of a surface crosslinking agent, wherein the polymerizable antimicrobial monomer comprises one or more of guanidine acrylate and salts thereof.

Furthermore, according to still another embodiment of the present invention, there is provided a hygiene product comprising the superabsorbent polymer.

Advantageous Effects

A superabsorbent polymer of the present technology may exhibit excellent bacterial growth inhibitory property and deodorant property to selectively inhibit growth of bacteria which are harmful to the human body and cause secondary odor, such as *Proteus mirabilis*.

Further, the superabsorbent polymer may uniformly exhibit excellent bacterial growth inhibitory property and deodorant property for a long time by carrying out crosslinking polymerization of an ethylene-based unsaturated monomer and an antimicrobial monomer during formation of base polymer powder, and may maintain excellent water retention capacity and absorption under pressure without deterioration in physical properties due to addition of the antimicrobial agent.

Accordingly, the superabsorbent polymer may be very preferably applied to a variety of hygiene products, particularly, diapers for adults having a problem of secondary odor, etc.

BRIEF DESCRIPTION OF DRAWINGS

FIG. 1 is a graph showing the result of 1H NMR analysis of guanidine acrylate (GA) prepared in Preparation Example 1;

FIG. 2 is a graph showing the result of 1H NMR analysis of a salt (GAS) of guanidine acrylate prepared in Preparation Example 2;

FIG. 3 is a graph showing the result of 1H NMR analysis of guanidine methacrylate (MGU) prepared in Comparative Preparation Example 1; and FIG. 4 is a graph showing the result of 1H NMR analysis of a salt (GMA) of guanidine methacrylate prepared in Comparative Preparation Example 2.

DETAILED DESCRIPTION OF THE EMBODIMENTS

The terms used in this description are just for explaining exemplary embodiments and it is not intended to restrict the present invention. The singular expression may comprise the plural expression unless it is differently expressed contextually. It must be understood that the term "comprise", "equip", or "have" in the present description is only used for designating the existence of characteristics taken effect, steps, components, or combinations thereof, and do not exclude the existence or the possibility of addition of one or more different characteristics, steps, components or combinations thereof beforehand.

In the present disclosure, alkyl having 1 to 20 carbon atoms may be a linear, branched, or cyclic alkyl group. Specifically, an alkyl group having 1 to 20 carbon atoms may be a linear alkyl group having 1 to 18 carbon atoms; a linear alkyl group having 1 to 10 carbon atoms; a linear alkyl group having 1 to 5 carbon atoms; a branched or cyclic alkyl group having 3 to 20 carbon atoms; a branched or cyclic alkyl group having 3 to 18 carbon atoms; or a branched or cyclic alkyl group having 3 to 10 carbon atoms. Specific examples thereof may comprise a methyl group, an ethyl group, an n-propyl group, an iso-propyl group, an n-butyl group, an iso-butyl group, a tert-butyl group, an n-pentyl group, an iso-pentyl group, a neo-pentyl group, a cyclohexyl group, etc., but are not limited thereto.

The present invention may be variously modified and have various forms, and specific examples are exemplified and explained in detail below. However, it is not intended to limit the present invention to the specific examples, and it must be understood that the present invention comprises every modifications, equivalents, or replacements included in the spirit and technical scope of the present invention.

Hereinafter, a superabsorbent polymer and a preparation method thereof will be described in more detail according to specific embodiments of the present invention.

Traditionally, in order to secure antimicrobial and deodorant properties in a superabsorbent polymer, a metal compound having an antimicrobial function or an organic compound containing a cation or alcohol functional group has been introduced in the form of an additive. However, in this case, safety of the superabsorbent polymer is deteriorated, basic physical properties such as absorption properties, etc. are deteriorated, and there are also problems in persistence of antimicrobial properties and leakage of antimicrobial substances.

Accordingly, in the present technology, a polymerizable antimicrobial monomer having an ethylenically unsaturated functional group together with an antimicrobial agent-derived structure was prepared, and the antimicrobial substance was incorporated into the polymer chain of a superabsorbent polymer using the same. As a result, it was confirmed that the superabsorbent polymer may continuously exhibit excellent growth inhibitory and deodorant properties for a long time with respect to odor-causing bacteria existing in the human skin without deteriorating basic physical properties of the superabsorbent polymer, such as water retention capacity, absorption under pressure, etc., and there is no concern about the leakage of antimicrobial substances, thereby improving safety for the human body. Therefore, it was confirmed that the superabsorbent polymer may be very preferably applied to a variety of hygiene products, such as diapers for adults, in which secondary odor is particularly problematic.

Specifically, the superabsorbent polymer according to one embodiment of the present invention may comprise a base polymer powder comprising a crosslinked polymer of water-soluble ethylene-based unsaturated monomers having acidic groups of which at least a part are neutralized, and a polymerizable antimicrobial monomer; and a surface crosslinked layer formed on the base polymer powder, in which the crosslinked polymer is additionally crosslinked by a surface crosslinking agent;

wherein the polymerizable antimicrobial monomer comprises one or more of guanidine acrylate and salts thereof.

With regard to the superabsorbent polymer, the crosslinked polymer is prepared by carrying out crosslinking polymerization of the water-soluble ethylene-based unsaturated monomers having acidic groups of which at least a part are neutralized, and the polymerizable antimicrobial monomer in the presence of an internal crosslinking agent, wherein main chains formed by polymerization of the monomers have a three-dimensional network structure crosslinked by the internal crosslinking agent. The structure derived from the polymerizable antimicrobial monomer is comprised as a repeating unit in the main chain constituting the crosslinked polymer, thereby exhibiting excellent antimicrobial property.

Specifically, the crosslinked polymer comprises a guanidine moiety derived from guanidine acrylate or a salt thereof as the polymerizable antimicrobial monomer. The guanidine moiety physicochemically destroys the cell surface structure of bacteria, and inhibits growth of bacteria by inducing protein denaturation due to its strong positive charge property. As a result, the superabsorbent polymer may exhibit antimicrobial property. In addition, the crosslinked polymer comprises a structure derived from an acrylate group, which is a polymerizable reactive group of a polymerizable antimicrobial monomer. As compared with a common polymerizable reactive group, in particular, a methacrylate group, the acrylate group minimizes the steric hinderance of the molecule to allow the guanidine moiety to be more freely in contact with the surface layer of bacterial cells. As a result, the antimicrobial property of the guanidine moiety may be further improved.

In addition, the guanidine moiety in the polymerizable antimicrobial monomer exhibits a strong electrostatically positive charge, thereby exhibiting an excellent growth inhibitory effect against Gram-negative bacteria among bacteria, particularly, *Proteus mirabilis*, which generates a secondary odor through generation of ammonia. As a result, the superabsorbent polymer may exhibit not only the excellent antimicrobial effect against *Proteus mirabilis*, but also a deodorant effect against odor caused by *Proteus mirabilis*, specifically, ammonia.

Further, since the polymerizable antimicrobial monomer does not exist as a separate compound in the superabsorbent polymer, but exists as a repeating unit constituting the main chain of the crosslinked polymer, it does not leak out over time, and therefore, the superabsorbent polymer may stably exhibit antimicrobial and deodorant effects for a long time.

The polymerizable antimicrobial monomer may be specifically guanidine acrylate or a salt thereof, and more specifically, a compound represented by the following Chemical Formula 1 or 2:

[Chemical Formula 1]

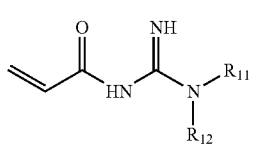

in Chemical Formula 1,
$R_{11}$ and $R_{12}$ are each independently hydrogen or an alkyl group having 1 to 20 carbon atoms, and

[Chemical Formula 2]

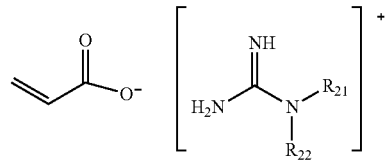

in Chemical Formula 2,
$R_{21}$ and $R_{22}$ are each independently hydrogen or an alkyl group having 1 to 20 carbon atoms.

In Chemical Formula 1, Ru and $R_{12}$ may be specifically each independently hydrogen or a linear or branched alkyl group having 1 to 6 carbon atoms, and more specifically, $R_{11}$ and $R_{12}$ may be each independently hydrogen or methyl.

Further, in Chemical Formula 2, $R_{21}$ and $R_{22}$ may be specifically each independently hydrogen or a linear or branched alkyl group having 1 to 6 carbon atoms, and more specifically, $R_{21}$ and $R_{22}$ may be each independently hydrogen or methyl.

Much more specifically, the polymerizable antimicrobial monomer may be a compound having the following structure, and of them, any one or a mixture of two or more thereof may be used:

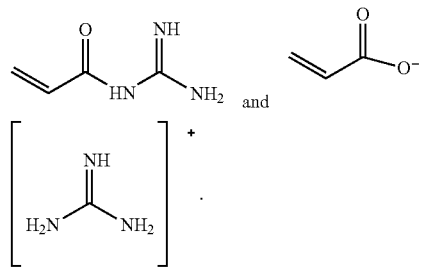

The polymerizable antimicrobial monomer is obtained by linking an acrylate group, which is a polymerizable functional group, to a guanidine-based compound, which is usually used as an antimicrobial agent, and may be prepared using a chemical reaction capable of introducing the acrylate group into the guanidine-based compound. For example, the polymerizable antimicrobial monomer may be prepared by reacting acrylic acid with a guanidine-based compound such as guanidine, guanidine carbonate, guanidine hydrochloride, etc. The method of preparing the polymerizable antimicrobial monomer is not particularly limited, and will be described in more detail in Preparation Examples below.

Meanwhile, in the superabsorbent polymer, the polymerizable antimicrobial monomer is included as a crosslinked polymer resulting from crosslinking polymerization with the water-soluble ethylene-based unsaturated monomer, and thus the antimicrobial and deodorant properties of the superabsorbent polymer may be further improved by controlling the content of the repeating unit derived from the polymerizable antimicrobial monomer. The content of the repeating unit derived from the polymerizable antimicrobial monomer may be controlled through the amount of the polymerizable antimicrobial monomer introduced during the polymerization reaction. Specifically, the polymerizable antimicrobial monomer may be used in an amount of 0.01 part by weight to 10 parts by weight with respect to 100 parts by weight of the water-soluble ethylene-based unsaturated monomer. When the content of the antimicrobial monomer is less than 0.01 part by weight, it is difficult to exhibit sufficient bacterial growth inhibitory property and deodorant property, and when the content of antimicrobial monomer is more than 10 parts by weight, there is a concern about deterioration in physical properties of the prepared superabsorbent polymer, such as absorbency, etc. More specifically, the polymerizable antimicrobial monomer may be used in an amount of 0.01 part by weight or more, 0.1 part by weight or more, 0.5 parts by weight or more, or 1 part by weight or more, and 10 parts by weight or less, 5 parts by weight or less, or 3 parts by weight or less.

Meanwhile, in the present technology, whether the repeating unit derived from the polymerizable antimicrobial monomer is included in the crosslinked polymer of the superabsorbent polymer may be confirmed by analyzing the presence of the nitrogen component included in the polymerizable antimicrobial monomer through EDS or nitrogen analysis of SEM.

Meanwhile, the superabsorbent polymer according to one embodiment of the present invention comprises a surface crosslinked layer which is obtained by additional crosslinking (secondary crosslinking) of the crosslinked polymer on the surface of the base polymer powder via a surface crosslinking agent, through treatment of the base polymer powder comprising the crosslinked polymer with the surface crosslinking agent. Therefore, the superabsorbent polymer exhibits higher crosslinking density on the surface thereof than inside thereof, and as a result, it may exhibit more excellent absorbency.

The above-described superabsorbent polymer may be prepared by a preparation method comprising the steps of: carrying out a crosslinking polymerization of water-soluble ethylene-based unsaturated monomers having acidic groups of which at least a part are neutralized, and a polymerizable antimicrobial monomer, in the presence of an internal crosslinking agent, to form a hydrogel polymer (step 1); drying, pulverizing, and classifying the hydrogel polymer to form a base polymer powder (step 2); and carrying out additional crosslinking of the base polymer powder by heat treatment in the presence of a surface crosslinking agent (step 3). According to another embodiment of the present invention, provided is a method of preparing the above-described superabsorbent polymer.

Hereinafter, each step will be described in detail.

First, the step 1 for preparing the superabsorbent polymer according to one embodiment of the present invention is a step of forming the hydrogel polymer.

Specifically, the hydrogel polymer may be prepared by carrying out a crosslinking polymerization of water-soluble ethylene-based unsaturated monomers having acidic groups of which at least a part are neutralized, and a polymerizable antimicrobial monomer, in the presence of an internal crosslinking agent. To this end, a monomer composition in a solution state, comprising the above-described monomers, a polymerization initiator, the internal crosslinking agent, and an aqueous solvent, may be used.

The polymerizable antimicrobial monomer is the same as described above, and may be used in an amount of 0.01 part by weight or more, 0.1 part by weight or more, 0.5 parts by weight or more, or 1 part by weight or more, and 10 parts by weight or less, 5 parts by weight or less, or 3 parts by weight or less, with respect to 100 parts by weight of the water-soluble ethylene-based unsaturated monomer.

Meanwhile, as the water-soluble ethylene-based unsaturated monomer for the preparation of the superabsorbent polymer, any monomer commonly used in the superabsorbent polymer may be used without particular limitation. Here, the monomer may be any one or more monomers selected from the group consisting of an anionic monomer and a salt thereof, a nonionic hydrophilic monomer, and an amino group-containing unsaturated monomer and a quaternary compound thereof.

Specifically, the monomer may comprise any one or more selected from the group consisting of an anionic monomer such as (meth)acrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methylpropane sulfonic acid, and a salt thereof a nonionic hydrophilic monomer such as (meth)acrylamide, N-substituted (meth)acrylate, 2-hydroxyethyl(meth)acrylate, 2-hydroxypropyl (meth)acrylate, methoxypolyethyleneglycol(meth)acrylate, or polyethyleneglycol(meth)acrylate; and an unsaturated monomer containing an amino group such as (N,N)-dimethylaminoethyl(meth)acrylate or (N,N)-dimethylaminopropyl(meth)acrylamide, and a quaternary compound thereof.

More preferably, acrylic acid or a salt thereof, for example, acrylic acid or an alkali metal salt thereof such as a sodium salt thereof may be used. When these monomers are used, it is possible to prepare a superabsorbent polymer having more excellent physical properties. When an alkali metal salt of acrylic acid is used as a monomer, acrylic acid may be used after being neutralized with a basic compound such as caustic soda (NaOH). In this regard, a degree of neutralization may be 40 mol % to 95 mol %, or 40 mol % to 80 mol %, or 45 mol % to 75 mol %. The range of the neutralization degree may vary depending on final physical properties. However, an excessively high degree of neutralization renders the neutralized monomers precipitated, and thus polymerization may not occur readily. On the contrary, an excessively low degree of neutralization not only greatly deteriorates absorbency of the polymer but also endows the polymer with hard-to-handle properties, such as of elastic rubber.

Further, the internal crosslinking agent is for internal crosslinking of the polymer which is obtained by polymerizing the acrylic acid-based monomer and the polymerizable antimicrobial monomer, and it is distinguished from a surface crosslinking agent for surface-crosslinking of the polymer.

The internal crosslinking agent may comprise a crosslinking agent having one or more ethylenic unsaturated groups in addition to one or more functional groups capable of reacting with water-soluble substituents of the water-soluble ethylene-based unsaturated monomer; or a crosslinking agent having two or more functional groups capable of reacting with the water-soluble substituents of the monomer and/or the water-soluble substituents formed by hydrolysis of the monomer.

Specific examples of the internal crosslinking agent may comprise one or more selected from the group consisting of bisacrylamide having 8 to 12 carbon atoms, bismethacrylamide, poly(meth)acrylate of a polyol having 2 to 10 carbon atoms, poly(meth)allyl ether of a polyol having 2 to 10 carbon atoms, etc. More specific examples thereof may comprise one or more selected from the group consisting of N,N'-methylene bis(meth)acrylate, ethyleneoxy(meth)acrylate, polyethyleneoxy(meth)acrylate, propyleneoxy(meth) acrylate, glycerin diacrylate, glycerin triacrylate, trimethyloltriacrylate, triallylamine, triarylcyanurate, triallylisocyanate, polyethylene glycol diacrylate, polyethylene glycol, diethylene glycol, and propylene glycol.

Such an internal crosslinking agent may be included in an amount of 0.01 part by weight to 1 part by weight with respect to 100 parts by weight of the water-soluble ethylene-based unsaturated monomer, thereby crosslinking the polymerized polymer. When the content of the internal crosslinking agent is less than 0.01 part by weight, the improvement effect due to crosslinking is insufficient, and when the content of the internal crosslinking agent is more than 1 part by weight, absorbency of the superabsorbent polymer may decrease. More specifically, the internal crosslinking agent may be included in an amount of 0.05 parts by weight or more, or 0.1 part by weight or more, and 0.5 parts by weight or less, or 0.3 parts by weight or less with respect to 100 parts by weight of the water-soluble ethylene-based unsaturated monomer.

In addition, a polymerization initiator may be further introduced during the crosslinking polymerization.

Specifically, the polymerization initiator may be a photopolymerization initiator by UV irradiation. However, even though the photopolymerization method is used, a certain amount of heat is generated by ultraviolet irradiation, etc., and a certain amount of heat is generated in accordance with the progression of the polymerization reaction, which is an exothermic reaction, and therefore, a thermal polymerization initiator may be further included.

The photopolymerization initiator may be used without limitation in view of constitution, as long as it is a compound capable of forming a radical by light such as UV ray.

The photopolymerization initiator may include, for example, one or more initiators selected from the group consisting of benzoin ether, dialkyl acetophenone, hydroxyl alkylketone, phenyl glyoxylate, benzyl dimethyl ketal, acyl phosphine, and α-aminoketone. Meanwhile, specific examples of the acyl phosphine may comprise commercially available lucirin TPO, namely, diphenyl(2,4,6-trimethylbenzoyl)-phosphine oxide. More various photopolymerization initiators are well disclosed in "UV Coatings: Basics, Recent Developments and New Application (Elsevier 2007)" written by Reinhold Schwalm, p 115, however, the photopolymerization initiator is not limited to the above-described examples.

The photopolymerization initiator may be included in an amount of 0.001 part by weight to 1 part by weight with respect to 100 parts by weight of the water-soluble ethylene-based unsaturated monomer. When the content of the photopolymerization initiator is less than 0.001 part by weight, the polymerization rate may become slow, and when the content of the photopolymerization initiator is more than 1 part by weight, a molecular weight of the superabsorbent polymer becomes small, and its physical properties may become uneven. More specifically, the photopolymerization initiator may be included in an amount of 0.005 parts by weight or more, 0.01 part by weight or more, or 0.1 part by weight or more, and 0.5 parts by weight or less, or 0.3 parts by weight or less with respect to 100 parts by weight of the water-soluble ethylene-based unsaturated monomer.

In addition, when the thermal polymerization initiator is further included as the polymerization initiator, the thermal polymerization initiator may comprise one or more selected from the group consisting of a persulfate-based initiator, an azo-based initiator, hydrogen peroxide, and ascorbic acid. Specifically, examples of the persulfate-based initiator may comprise sodium persulfate ($Na_2S_2O_8$), potassium persulfate ($K_2S_2O_8$), ammonium persulfate ($(NH_4)_2S_2O_8$), etc., and examples of the azo-based initiator may comprise 2,2-azobis-(2-amidinopropane)dihydrochloride, 2,2-azobis-(N,N-dimethylene)isobutyramidine dihydrochloride, 2-(carbamoylazo)isobutyronitrile, 2,2-azobis[2-(2-imidazolin-2-yl)propane]dihydrochloride, 4,4-azobis-(4-cyanovaleric acid), etc. More various thermal polymerization initiators are well disclosed in 'Principle of Polymerization (Wiley, 1981)' written by Odian, p 203, however, the thermal polymerization initiator is not limited to the above-described examples.

The thermal polymerization initiator may be included in an amount of 0.001 part by weight to 1 part by weight with respect to 100 parts by weight of the water-soluble ethylene-based unsaturated monomer. When the content of the thermal polymerization initiator is less than 0.001 part by weight, additional thermal polymerization hardly occurs, and thus effects due to the addition of the thermal polymerization initiator may be insufficient, and when the content of the thermal polymerization initiator is more than 1 part by weight, the molecular weight of the superabsorbent polymer becomes small, and the physical properties may become uneven. More specifically, the thermal polymerization initiator may be included in an amount of 0.005 parts by weight or more, 0.01 part by weight or more, or 0.1 part by weight or more, and 0.5 parts by weight or less, or 0.3 parts by weight or less with respect to 100 parts by weight of the water-soluble ethylene-based unsaturated monomer.

In addition to the above polymerization initiators, one or more additives, such as a surfactant, a thickener, a plasticizer, a preservation stabilizer, an antioxidant, etc., may be further included, as needed in the crosslinking polymerization.

The monomer composition comprising the above-described water-soluble ethylene-based unsaturated monomer, polymerizable antimicrobial monomer, and internal crosslinking agent, and optionally, the photopolymerization initiator, and the additive may be prepared in the form of a solution, in which the monomer composition is dissolved in a solvent.

As the solvent to be applicable, any solvent may be used without limitations in view of constitution as long as it is able to dissolve the above components, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide may be used in combination. The solvent may be included in a residual amount excluding the above-described components from the total weight of the monomer composition.

When an aqueous solvent, such as water, is used as the solvent, and a terpene-based compound showing no solubility for water is used as the polymerizable antimicrobial monomer, a surfactant may be additionally introduced in an amount of 10 parts by weight or less with respect to 100 parts by weight of the polymerizable antimicrobial monomer, in order to increase the solubility.

Meanwhile, the method of forming the hydrogel polymer by carrying out photopolymerization of the monomer composition is also not particularly limited in view of constitution, as long as it is a polymerization method commonly used.

Specifically, the photopolymerization may be carried out by irradiating ultraviolet ray with an intensity of 5 mW to 30 mW, or 10 mW to 20 mW at a temperature of 60° C. to 90° C., or 70° C. to 80° C. When the photopolymerization is carried out under the above conditions, it is possible to form the crosslinked polymer with higher polymerization efficiency.

When the photopolymerization is carried out, it may be carried out in a reactor equipped with a movable conveyor belt. The above-described polymerization method is only an example, and the present invention is not limited to the above-described polymerization method.

In addition, when the photopolymerization is carried out in a reactor equipped with a movable conveyor belt, the obtained hydrogel polymer may be usually a sheet-like hydrogel polymer having a width of the belt. In this case, the thickness of the polymer sheet may vary depending on the concentration of the monomer composition fed thereto and the feeding speed. Usually, the monomer composition is preferably introduced such that a sheet-like polymer having a thickness of about 0.5 cm to about 5 cm may be obtained. When the monomer composition is introduced to such an extent that the thickness of the sheet-like polymer becomes too thin, it is undesirable because the production efficiency is low, and when the thickness of the sheet-like polymer is more than 5 cm, the polymerization reaction may not evenly occur over the entire thickness because of the excessive thickness.

The hydrogel polymer obtained by the above-mentioned method may have a water content of 40% by weight to 80% by weight with respect to the total weight of the hydrogel polymer. Meanwhile, the "water content" as used herein means a weight occupied by water with respect to the total weight of the hydrogel polymer, which may be a value obtained by subtracting the weight of the dried polymer from the weight of the hydrogel polymer. Specifically, the water content may be defined as a value calculated by measuring the weight loss due to evaporation of moisture in the polymer during the process of drying by raising the temperature of the polymer through infrared heating. At this time, the water content is measured under the drying conditions determined as follows: the drying temperature is increased from room temperature to about 180° C. and then the temperature is maintained at 180° C., and the total drying time is set to 20 minutes, comprising 5 minutes for the temperature rising step.

Meanwhile, after preparing the hydrogel polymer, a process of coarsely pulverizing the prepared hydrogel polymer may be optionally carried out, prior to subsequent drying and pulverizing processes.

The coarsely pulverizing is a process for increasing the drying efficiency in the subsequent drying process and controlling the particle size of the final superabsorbent polymer powder, and a pulverizer used here is not limited by its configuration, and specifically, it may comprise any one selected from the group consisting of a vertical pulverizer, a turbo cutter, a turbo grinder, a rotary cutter mill, a cutter mill, a disc mill, a shred crusher, a crusher, a meat chopper, and a disc cutter, but is not limited to the above-described examples.

For example, the coarsely pulverizing may be carried out such that the particle size of the hydrogel polymer becomes about 2 mm to about 10 mm. When the hydrogel polymer is pulverized into a particle size of less than 2 mm, it is not technically easy due to its high water content, and an agglomeration phenomenon between the pulverized particles may occur. Meanwhile, when the polymer is pulverized into a particle size of more than 10 mm, the effect of increasing the efficiency in the subsequent drying step may be insufficient.

Next, the step 2 is a step of forming the base polymer powder by drying, pulverizing, and classifying the hydrogel polymer prepared in the step 1.

As the drying method, any drying method may be selected and used without limitation in view of constitution, as long as it is commonly used in the process of drying the hydrogel polymer. Specifically, the drying step may be carried out by a method such as hot air supply, infrared irradiation, microwave irradiation, or ultraviolet irradiation.

Specifically, the drying may be carried at a temperature of about 150° C. to about 250° C. When the drying temperature is lower than 150° C., there is a concern about excessively extended drying time or deterioration of the physical properties of the final superabsorbent polymer, and when the drying temperature is higher than 250° C., only the surface of the polymer is dried, and thus there is a concern about generation of fine particles during the subsequent pulverization process or deterioration of the physical properties of the final superabsorbent polymer. Therefore, the drying may be preferably performed at a temperature of 150° C. or higher, or 160° C. or higher, and 200° C. or lower, or 180° C. or lower.

Meanwhile, the drying may be carried out for about 20 minutes to about 90 minutes, in consideration of the process efficiency, but is not limited thereto.

When the drying step as above is finished, the water content of the polymer may be about 5% by weight to about 10% by weight.

After the drying process, a pulverizing process is carried out.

The pulverizing process may be carried out such that the polymer powder, i.e., base polymer powder may have a particle size of about 150 μm to about 850 μm. Specific examples of a pulverizer that may be used to achieve the above particle size may comprise a pin mill, a hammer mill, a screw mill, a roll mill, a disc mill, a jog mill, etc., but the present invention is not limited to the above-described examples.

After the pulverization step, in order to manage physical properties of the finally commercialized superabsorbent polymer powder, the pulverized polymer powder may be classified according to the particle size.

Preferably, the polymer powder is classified into polymers having a particle size of about 150 μm to about 850 μm, and only the polymer having such a particle size may be used as the base polymer powder to be commercialized through a surface crosslinking step.

The base polymer powder resulting from the above-described processes may be in the form of fine powder comprising the crosslinked polymer which is obtained by crosslinking polymerization of the water-soluble ethylene-based unsaturated monomer and the polymerizable antimicrobial monomer via the internal crosslinking agent. Specifically, the base polymer powder may be in the form of fine powder having a particle size of 150 μm to 850 μm.

Next, the step 3 is a step of carrying out additional crosslinking (surface crosslinking) of the base polymer powder prepared in the step 2 by heat treatment in the presence of a surface crosslinking agent.

The additional crosslinking is to increase a crosslinking density near the surface of the base polymer powder in relation to a crosslinking density inside the particle. In general, the surface-crosslinking agent is applied to the surface of the base polymer powder. Thus, this reaction is generated on the surface of the base polymer powder, which improves crosslinkability on the surface of the particles without substantially affecting the inside of the particles. Thus, surface-crosslinked base polymer powder has a higher crosslinking degree in the vicinity of the surface than in the inside thereof, and as a result, it may exhibit more improved absorption under pressure, as compared with those without a surface-crosslinked layer. Meanwhile, when the surface crosslinked layer is not formed, gel strength may be increased to improve absorption under pressure. However, when a superabsorbent polymer with increased gel strength without forming the surface crosslinked layer is applied to an absorbent article, the gel breaks if a pressure is applied thereto, and thus microorganisms absorbed into the absorbent article are exposed to the outside, causing secondary contamination. However, when the surface crosslinked layer is formed as described above, even if a pressure is applied to the gel, the shape of the gel is well maintained, thereby preventing microorganisms absorbed during use from being exposed to the outside.

The additional crosslinking step may be carried out using a surface crosslinking solution comprising the surface crosslinking agent and an aqueous solvent.

The surface crosslinking agent is not limited in view of constitution, as long as it is a compound reactable with functional groups of the polymer. Preferably, to improve properties of the prepared superabsorbent polymer, the surface crosslinking agent may comprise one or more selected from the group consisting of a polyhydric alcohol compound; an epoxy compound; a polyamine compound; a haloepoxy compound; a condensation product of a haloepoxy compound; oxazoline compounds; mono-, di- or polyoxazolidinone compound; a cyclic urea compound; a polyvalent metal salt; and an alkylene carbonate compound.

Specific examples of the polyhydric alcohol compound may comprise one or more selected from the group consisting of ethylene glycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, and glycerol.

Further, the epoxy compound may comprise ethylene glycol diglycidyl epoxide, ethylene glycol diglycidyl ether, glycidol, etc., and the polyamine compounds may comprise one or more selected from the group consisting of ethylene diamine, diethylene triamine, triethylene tetramine, tetraethylene pentamine, pentaethylene hexamine, polyethylene imine, and polyamide polyamine.

Further, the haloepoxy compound may be epichlorohydrin, epibromohydrin, and α-methyl epichlorohydrin. Meanwhile, examples of the mono-, di- or polyoxazolidinone compound may comprise 2-oxazolidinone, etc.

The alkylene carbonate compound may comprise alkylene carbonate having 2 to 6 carbon atoms, such as ethylene carbonate, propylene carbonate, etc. These compounds may be used alone or in combination of two or more of alkylene carbonates which are different in the number of carbon atoms.

Further, the polyvalent metal salt may be specifically sulfate or carboxylate containing a metal such as aluminum, etc., and among them, aluminum sulfate may be more preferably used.

The surface crosslinking agent may be introduced in an amount of 0.001 part by weight to 5 parts by weight with respect to 100 parts by weight of the base polymer powder. For example, the surface crosslinking agent may be used in an amount of 0.005 parts by weight or more, 0.01 part by weight or more, or 0.1 part by weight or more, and 3 parts by weight or less, 2 parts by weight or less, or 1 part by weight or less with respect to 100 parts by weight of the base polymer powder. By controlling the content of the surface crosslinking agent within the above-described range, it is possible to prepare a superabsorbent polymer showing excellent overall properties such as absorption performances, liquid permeability, etc. When the content of the surface crosslinking agent is too low, the surface crosslinking reaction hardly occur, and when the content of the surface crosslinking agent exceeds 5 parts by weight with respect to 100 parts by weight of the base polymer powder, absorption performances and physical properties may deteriorate due to excessive surface crosslinking reaction.

The method of mixing the surface crosslinking agent with the base polymer powder is not limited in view of constitution. A method of adding and mixing the surface crosslinking agent and the base polymer powder in a reactor, a method of spraying the surface crosslinking agent onto the base polymer powder, a method of continuously feeding the base polymer powder and the surface crosslinking agent to a mixer which is continuously operated, etc. may be used.

In addition to the surface crosslinking agent, water and alcohol may be mixed together, and the mixture may be added in the form of a surface crosslinking solution. When water and alcohol are added, there is an advantage in that the surface crosslinking agent may be evenly distributed in the base polymer powder. In this regard, the amounts of water and alcohol to be added may be preferably about 5 parts by weight to about 12 parts by weight with respect to 100 parts by weight of the polymer for the purpose of inducing uniform dispersion of the surface crosslinking agent, preventing agglomeration of base polymer powder, and at the same time, optimizing the surface penetration depth of the surface crosslinking agent.

Further, the surface crosslinking reaction may occur by heating the base polymer powder, to which the surface crosslinking agent is added, at a temperature of about 80° C. to about 220° C. for about 15 minutes to about 100 minutes. When the crosslinking reaction temperature is lower than 80° C., sufficient surface crosslinking reaction may not occur, and when the crosslinking reaction temperature is higher than 220° C., excessive surface crosslinking reaction may occur. In addition, when the crosslinking reaction time is shorter than 15 minutes, sufficient surface crosslinking reaction may not occur, and when the crosslinking reaction time exceeds 100 minutes, excessive surface crosslinking reaction may occur, and thus crosslinking density of the particle surface becomes too high, leading to deterioration in the physical properties. More specifically, the surface crosslinking reaction may be carried out by heating at a temperature of 120° C. or higher, or 140° C. or higher, and 200° C. or lower, or 180° C. or lower for 20 minutes or longer, or 40 minutes or longer, and 70 minutes or less, or 60 minutes or less.

A means for raising the temperature for the additional crosslinking reaction is not particularly limited. Heating may be performed by providing a heating medium or by directly providing a heat source. In this regard, the kind of the heating medium applicable may be steam, hot air, a hot fluid such as hot oil or the like, but the present invention is not limited thereto. The temperature of the heating medium to be provided may be properly controlled, taking into consideration the means of the heating medium, the heating rate, and the target temperature. Meanwhile, as the heat source to be directly provided, an electric heater or a gas heater may be used, but the present invention is not limited to these examples.

The superabsorbent polymer prepared according to the above-described preparation method comprises the base polymer powder comprising the crosslinked polymer of the water-soluble ethylene-based unsaturated monomer and the polymerizable antimicrobial monomer, and a surface crosslinked layer which is formed on the base polymer powder and is prepared by further crosslinking the crosslinked polymer of the base polymer powder via a surface crosslinking agent. By comprising the structure unit derived from the antimicrobial monomer in the crosslinked polymer, the superabsorbent polymer may continuously and safely exhibit improved bacterial growth inhibitory property and deodorant property without deterioration in physical properties of the superabsorbent polymer, such as water retention capacity, absorption under pressure, etc.

Specifically, the superabsorbent polymer may have 30-min centrifuge retention capacity (CRC) of about 29 g/g to 50 g/g for a physiological saline solution (0.9 wt % aqueous sodium chloride solution), as measured in accordance with EDANA method WSP 241.3. As the superabsorbent polymer has CRC within the above range, there is no concern about deterioration of absorption under pressure which has a trade-off relationship with the water retention capacity, and as a result, it is appropriately applied to hygiene products. More specifically, CRC of the superabsorbent polymer is 29 g/g or more, or 30 g/g or more, and 50 g/g or less, or 40 g/g or less.

Further, the superabsorbent polymer exhibits excellent bacterial growth inhibitory effect, i.e., a bacterial growth rate of 20% or less, and more specifically, 12% or less, or 5% or less, as calculated according to the following Equation 1, when the superabsorbent polymer is injected into artificial urine, in which 3000 CFU/ml of bacteria are inoculated, and then incubated at 35° C. for 12 hours.

Bacterial growth rate (%)=[$CFU_{sample}$/$CFU_{reference}$]× 100   [Equation 1]

In Equation 1, $CFU_{reference}$ represents CFU of bacteria after being cultured with a superabsorbent polymer without the polymerizable antimicrobial monomer, and $CFU_{sample}$ represents CFU of bacteria after being cultured with the superabsorbent polymer with the polymerizable antimicrobial monomer.

Further, the superabsorbent polymer comprises the antimicrobial monomer which is polymerized and incorporated into the crosslinked polymer, and thus the antimicrobial monomer hardly leaks out. Specifically, when the superabsorbent polymer is shaken with a physiological saline solution (0.9 wt % aqueous sodium chloride solution) for 1 hour, a liquid extract is filtered, and then the amount of the antimicrobial monomer that leaks into the liquid extract is measured by HPLC/PDA/MS or HPLC/CAD, the concentration of the polymerizable antimicrobial monomer in the liquid extract is 1 ppm or less, 0.4 ppm or less, or 0.2 ppm or less, based on the calibration curve of the polymerizable antimicrobial monomer. As described, since the antimicrobial monomer hardly leak out, excellent antimicrobial properties may be maintained. A method of measuring the concentration of the polymerizable antimicrobial monomer that leaks into the liquid extract will be specifically described in Experimental Example below.

In addition, the superabsorbent polymer exhibits excellent deodorant property, which may be confirmed by measuring the amount of ammonia generated in the bacterial culture solution using an ammonia detection tube after injecting and culturing artificial urine, in which the test bacteria are inoculated. The amount of ammonia was remarkably reduced, as compared with the amount of ammonia generated in the pure bacterial culture without the antimicrobial monomer.

Accordingly, the superabsorbent polymer may be preferably included and used in a variety of hygiene products, e.g., disposable diapers for children, diapers or sanitary pads for adults. In particular, the superabsorbent polymer may be very preferably applied to diapers for adults, in which secondary odor caused by bacterial growth is particularly problematic.

Such hygiene products may follow the configuration of a common hygiene product, except that the superabsorbent polymer of one embodiment is included in an absorber.

Hereinafter, preferred examples will be provided for better understanding of the present invention. However, the following examples are provided only for understanding the present invention, but the present invention is not limited thereby.

Preparation of Polymerizable Antimicrobial Monomer

Preparation Example 1

100 parts by weight of water was mixed with 19 parts by weight of acrylic acid, 10.8 parts by weight of guanidine hydrochloride, and 20 parts by weight of sodium methoxide, and then allowed to react under stirring at room temperature for 15 hours. When the reaction was terminated, acetone was added to the resulting solution to remove a white by-product (NaCl), followed by filtering using a filter. Acetone was removed from the resulting filtrate at room temperature using a rotary evaporator to obtain guanidine acrylate (GA) (i) having the following structure as a polymerizable antimicrobial monomer.

The obtained polymerizable antimicrobial monomer existed in the state of being dissolved in water, and its concentration was 1 g/10 ml. Further, the result of $^1$H NMR analysis of the obtained polymerizable antimicrobial monomer is shown in FIG. 1 (500 MHz, DMSO-$d_6$, δ[ppm]).

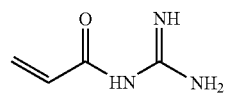

(i)

Preparation Example 2

100 parts by weight of water was mixed with 19 parts by weight of acrylic acid, and 14.4 parts by weight of guanidine carbonate, and then allowed to react under stirring at room temperature for 15 hours. When the reaction was terminated, the solvent was completely removed from the resulting solution using a rotary evaporator, and acetone was added thereto, followed by recrystallization. Then, filtration was performed using a filter to obtain a salt of guanidine acrylate (GAS) (ii) having the following structure as a polymerizable antimicrobial monomer. The obtained polymerizable antimicrobial monomer was in the form of a solid, and if necessary, used after being dissolved in water at the same concentration as in Preparation Example 1.

Further, the result of $^1$H NMR analysis of the obtained polymerizable antimicrobial monomer is shown in FIG. 2 (500 MHz, DMSO-d$_6$, δ[ppm]).

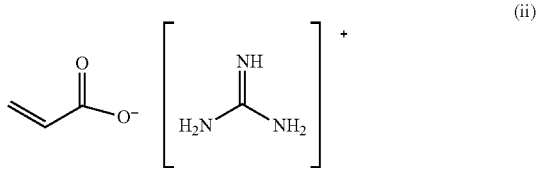

Comparative Preparation Example 1

The same method as in Preparation Example 1 was carried out, except that 9.5 parts by weight of methyl methacrylate was used instead of acrylic acid in Preparation Example 1, thereby obtaining an antimicrobial monomer (iii) of guanidine methacrylate (MGU) having the following structure. The obtained antimicrobial monomer existed in the state of being dissolved in water, and its concentration was 2 μg/10 ml.

Further, the result of $^1$H NMR analysis of the obtained polymerizable antimicrobial monomer is shown in FIG. 3 (500 MHz, DMSO-d$_6$, δ[ppm]).

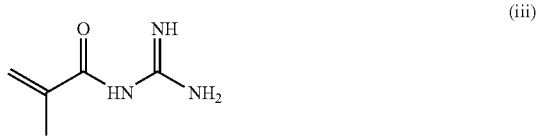

Comparative Preparation Example 2

The same method as in Preparation Example 2 was carried out, except that 18 parts by weight of methacrylic acid was used instead of acrylic acid in Preparation Example 2, thereby obtaining a salt of guanidine methacrylate (GMA) (iv) having the following structure as a polymerizable antimicrobial monomer. The obtained polymerizable antimicrobial monomer was in the form of a solid, and if necessary, used after being dissolved in water at the same concentration as in Preparation Example 1. Further, the result of $^1$H NMR analysis of the obtained polymerizable antimicrobial monomer is shown in FIG. 4 (500 MHz, DMSO-d$_6$, δ[ppm]).

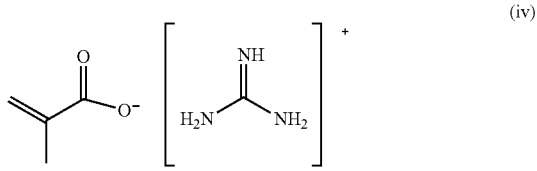

Preparation of Superabsorbent Polymer

Example 1

100 parts by weight of acrylic acid, 0.23 parts by weight of polyethylene glycol diacrylate (Mn=575) as an internal crosslinking agent, 0.008 parts by weight of bis(2,4,6-trimethylbenzoyl)-phenylphosphine oxide as a photoinitiator, 0.12 parts by weight of sodium persulfate (SPS) as a thermal initiator, 39.7 parts by weight of 98% sodium hydroxide solution, and 1 part by weight of guanidine acrylate (GA) prepared in Preparation Example 1 were put in a 3 L glass container equipped with an agitator, a nitrogen injector, and a thermometer, and a water-soluble unsaturated monomer aqueous solution was prepared by continuously adding nitrogen.

The water-soluble unsaturated monomer aqueous solution was put in a stainless-steel container having a width of 250 mm, a length of 250 mm, and a height of 30 mm, and then irradiated with ultraviolet rays in a UV chamber at 80° C. for 60 seconds (UV dose: 10 mV/cm$^2$), and aged for 2 minutes to obtain a hydrogel polymer.

After pulverizing the obtained hydrogel polymer into a size of 3 mm×3 mm, the obtained gel-type polymer was spread on a stainless wire gauze having a pore size of 600 μm at a thickness of about 30 mm, and dried in a hot air oven at 120° C. for 10 hours. The dried polymer thus obtained was pulverized using a pulverizer, and classified using a standard mesh of ASTM standard to obtain a base polymer powder having a particle size of 150 μm to 850 μm.

A surface crosslinking solution comprising 5.4 parts by weight of water, 1.2 parts by weight of ethylene carbonate, 0.2 parts by weight of propylene glycol, 0.2 parts by weight of polycarboxylic acid surfactant, and 0.2 parts by weight of aluminum sulfate was sprayed onto 100 parts by weight of the base polymer, and then mixed, and the mixture was placed in a container consisting of a stirrer and a double jacket to allow a surface crosslinking reaction at 180° C. for 70 minutes. Thereafter, the surface-treated powder was classified using a standard mesh of ASTM standard to obtain a superabsorbent polymer powder having a particle size of 150 μm to 850 μm.

Example 2

A superabsorbent polymer was prepared in the same manner as in Example 1, except that 2 parts by weight of guanidine acrylate was added in Example 1.

Example 3

A superabsorbent polymer was prepared in the same manner as in Example 2, except that the salt of guanidine acrylate (GAS) prepared in Preparation Example 2 was used instead of guanidine acrylate in Example 2.

Comparative Example 1

A superabsorbent polymer was prepared in the same manner as in Example 1, except that no polymerizable antimicrobial monomer was used in Example 1.

Comparative Example 2

A superabsorbent polymer was prepared in the same manner as in Example 2, except that the salt of guanidine methacrylate (GMA) prepared in Comparative Preparation Example 2 was used instead of guanidine acrylate in Example 2.

Comparative Example 3

A superabsorbent polymer was prepared in the same manner as in Example 2, except that the guanidine methacrylate (MGU) prepared in Comparative Preparation Example 1 was used instead of guanidine acrylate in Example 2.

Comparative Example 4

100 parts by weight of the superabsorbent polymer prepared in Comparative Example 1 was simply mixed with 2 parts by weight of the guanidine acrylate (GA) prepared in Preparation Example 1 (mixed at a ratio equivalent to the antimicrobial monomer used in the superabsorbent polymer prepared in Example 1).

Experimental Example 1

Physical properties were evaluated for the superabsorbent polymers prepared in Examples and Comparative Examples by the following methods.

Unless otherwise indicated, all the following physical properties were evaluated at constant temperature and humidity (23±1° C., relative humidity of 50±10%), and physiological saline or brine means a 0.9 wt % aqueous sodium chloride (NaCl) solution.

(1) Centrifuge Retention Capacity (CRC)

The centrifuge retention capacity (CRC) by absorbency under no load was measured for each of the superabsorbent polymers of Examples and Comparative Examples in accordance with European Disposables and Nonwovens Association (EDANA) standard EDANA WSP 241.3.

In detail, the superabsorbent polymer $W_0$ (g, about 2.0 g) was uniformly placed into a nonwoven-fabric-made bag, followed by sealing. Then, the bag was immersed at room temperature in a physiological saline solution (0.9 wt % aqueous sodium chloride solution). After 30 minutes, the bag was drained at 250 G for 3 minutes with a centrifuge, and the weight $W_2$ (g) of the bag was then measured. Further, the same procedure was carried out without the superabsorbent polymer, and the resultant weight $W_1$ (g) was measured. From these weights thus obtained, CRC (g/g) was calculated according to the following Equation:

$$CRC(g/g)=\{[W_2(g)-W_1(g)]/W_0(g)\}-1 \quad [\text{Equation 2}]$$

in Equation 2, $W_0(g)$ is the initial weight (g) of the superabsorbent polymer, $W_1(g)$ is the weight of a bag, which was measured after the bag without the superabsorbent polymer was immersed in the saline solution for 30 minutes, and then drained using a centrifuge at 250 G for 3 minutes, and $W_2(g)$ is the weight of a bag comprising the superabsorbent polymer, which was measured after the bag comprising the superabsorbent polymer was immersed in the saline solution at room temperature for 30 minutes, and then drained using a centrifuge at 250 G for 3 minutes.

(2) Evaluation of Antimicrobial Property Against *Proteus mirabilis*

50 ml of artificial urine, in which 3000 CFU/ml of *Proteus Mirabilis* (ATCC 29906) was inoculated, was incubated in a 35° C. incubator for 12 hours. The artificial urine immediately after inoculation of bacteria and the artificial urine after 12 hours were used as controls, washed well with 150 ml of brine (0.9 wt % aqueous sodium chloride solution), and cultured on a nutrient broth agar (BD DIFCO.) plate. CFU (Colony Forming Unit; CFU/ml) was measured and calculated as physical properties of the controls.

Each 2 g of the superabsorbent polymers of Examples or Comparative Examples was added to 50 ml of artificial urine, in which 3000 CFU/ml of *Proteus Mirabilis* (ATCC 29906) was inoculated, and incubated in a 35° C. incubator for 12 hours. 150 ml of brine (0.9 wt % aqueous sodium chloride solution) was added to the sample, of which incubation was completed, and the mixture was evenly mixed by shaking for 1 minute. The resulting diluted solution was plated on a nutrient broth agar (BD DIFCO.) plate, incubated in a 30° C. incubator for 24 hours, and then CFU (Colony Forming Unit; CFU/ml) was measured.

A bacterial growth rate of *Proteus Mirabilis* (ATCC 29906) represented by the following Equation 1 was calculated using the measurement results, and based on the bacterial growth rate, the bacterial growth inhibitory property of each of the superabsorbent polymers according to Examples and Comparative Examples was evaluated.

On the other hand, *Proteus Mirabilis*, which is a strain used to measure the bacterial growth rate, secretes urease. Urease breaks down urea in urine to generate ammonia, which causes odor. Therefore, the antimicrobial and deodorizing effects of the superabsorbent polymer may be appropriately evaluated by the growth rate of *Proteus Mirabilis*. Meanwhile, when growth of *Proteus Mirabilis* is excessively inhibited for the deodorant effect, it may cause problems such as skin rash by killing other bacteria beneficial to the human body. For this reason, it is necessary to inhibit the growth at an appropriate level.

$$\text{Bacterial growth rate (\%)}=[CFU_{sample}/CFU^{reference}]\times 100 \quad [\text{Equation 1}]$$

in Equation 1, $CFU_{reference}$ represents CFU of bacteria after being cultured with the superabsorbent polymer of Comparative Example 1 without the polymerizable antimicrobial monomer, and $CFU_{sample}$ represents CFU of bacteria after being cultured with the superabsorbent polymer of Example or Comparative Example with the polymerizable antimicrobial monomer.

(3) pH

To evaluate the inhibitory effect of the superabsorbent polymer on ammonia generation, 2 g of the superabsorbent polymer of Example or Comparative Example was added to 50 ml of artificial urine, to which 3000 CFU/ml of *Proteus Mirabilis* (ATCC 29906) was inoculated, and incubated in a 35° C. incubator for 12 hours. 150 ml of brine (0.9 wt % aqueous sodium chloride solution) was added to the sample, of which incubation was completed, and the mixture was evenly mixed by shaking for 1 minute. pH of the resulting diluted solution was measured using a pH meter.

When ammonia is generated during the culture of microorganisms, the generated ammonia is dissolved in artificial urine, and as a result, the artificial urine, of which pH is close to neutral or weak acidic, becomes basic, specifically, at pH of 8 or more.

(4) Evaluation of Leakage of Polymerizable Antimicrobial Monomer

It was confirmed whether the antimicrobial monomer was leaked out from the superabsorbent polymers prepared in Examples.

In detail, 20 ml of physiological saline (0.9 wt % aqueous sodium chloride solution) was added to 0.1 g of each superabsorbent polymer prepared in Examples and Comparative Examples, and shaken for 1 hour, and then each liquid extract was filtered. The extraction concentration of the leaked antimicrobial monomer was examined using HPLC/PDA/MS or HPLC/CAD according to the following conditions. Further, the polymerizable antimicrobial monomer used in Examples and Comparative Examples was dissolved in physiological saline (0.9 wt % aqueous sodium chloride solution) at concentrations of 0.2 ppm, 0.5 ppm, 1 ppm, 2 ppm, 10 ppm, and 100 ppm to prepare samples. Each sample concentration was measured using HPLC/PDA/MS or HPLC/CAD under the same conditions as in the measurement of the extraction concentration of the antimicrobial monomer, and thus a calibration curve was obtained. HPLC/PDA/MS was used in measuring the concentrations of the leaked antimicrobial monomer and the calibration curve for the superabsorbent polymers of Examples 1 and 2 and Comparative Example 3, and HPLC/CAD was used in measuring the concentrations of the leaked antimicrobial monomer and the calibration curve for the superabsorbent polymers of Example 3 and Comparative Example 2. Based on the obtained calibration curve, the concentration of the extracted polymerizable antimicrobial monomer in the liquid extract was expressed as ppm, <HPLC/PDA/MS Chromatographic Conditions>
select chromatographic column: Trinity P2 column
specification: 4.6 mm ID×50 mm L, 3 μm
Mobile phase A: volume fraction=distilled water (100 v/v %)
Mobile phase B: 100 mM Ammonium formate (pH 3.8) 100 v/v %
Flow velocity 0.6 mL/min
column temperature 40° C.
sample injection volume: 50 μL
Gradient elution: as in Table 1 below.

TABLE 1

| Time | A(%) | B(%) |
|---|---|---|
| 0 | 10 | 90 |
| 10 | 0 | 100 |
| 10.01 | 90 | 10 |

Ionization: ESI ionization
Mode: SIM mode (m/z=60)
<HPLC/CAD Chromatographic Conditions>
select chromatographic column: Trinity P2 column
specification: 4.6 mm ID×50 mm L, 3 μm
Mobile phase A: volume fraction=distilled water (100 v/v %)
Mobile phase B: 100 mM Ammonium formate (pH 3.8) 100 v/v %
Flow velocity: 0.6 mL/min
column temperature: 40° C.
sample injection volume: 2 μL;
Gradient elution: as in Table 2 below.

TABLE 2

| Time | A(%) | B(%) |
|---|---|---|
| 0 | 10 | 90 |
| 10 | 0 | 100 |
| 10.01 | 90 | 10 |

[CAD analysis conditions]
GAS Pressure: 6.18 psi
Charger voltage: 2.27 kV
Charger current: 0.99 μA
Flow mode: Normal
Ion trap: 20.2 V.

The experimental results are shown in Table 3 below.

TABLE 3

| | Kind of antimicrobial monomer | Content of antimicrobial monomer (parts by weight[1]) | CRC (g/g) | CFU/ml (12 h) | Bacterial growth rate (%) | pH | Concentration of antimicrobial monomer in liquid extract (ppm) |
|---|---|---|---|---|---|---|---|
| Example 1 | GA | 1.0 | 34.9 | $1.54 \times 10^8$ | 2.8 | 6.12 | No leakage |
| Example 2 | GA | 2.0 | 33.8 | $6.59 \times 10^7$ | 1.2 | 6.03 | No leakage |
| Example 3 | GAS | 2.0 | 32.9 | $5.83 \times 10^8$ | 10.6 | 7.09 | 1 |
| Comparative Example 1 | — | — | 33.1 | $5.50 \times 10^9$ | 100 | 8.46 | — |
| Comparative Example 2 | GMA | 2.0 | 32.7 | $4.80 \times 10^9$ | 87.3 | 8.14 | 3.5 |
| Comparative Example 3 | MGU | 2.0 | 32.5 | $4.17 \times 10^9$ | 75.8 | 7.96 | No leakage |
| Comparative Example 4 (simple mixing) | GA | 2.0 | 33.0 | $1.15 \times 10^8$ | 2.1 | 6.00 | 16.7 |

In Table, parts by weight[1] is a relative weight ratio based on 100 parts by weight of acrylic acid monomer.

As an experimental result, the superabsorbent polymers of Examples 1 to 3 satisfied 30-min centrifuge retention capacity (CRC) of 29 g/g to 50 g/g for a physiological saline solution (0.9 wt % aqueous sodium chloride solution), as measured in accordance with EDANA method WSP 241.3, and at the same time, exhibited excellent antimicrobial property against *Proteus mirabilis* which is one of Gram-negative bacteria, as compared with the superabsorbent polymers of Comparative Examples 1 to 3. Further, due to the excellent antimicrobial effect of the superabsorbent polymers of Examples 1 to 3, ammonia generation was reduced, and thus pH of the artificial urine was hardly increased. In contrast, when the superabsorbent polymers of Comparative Examples 1 to 3 were used, a large amount of ammonia was produced, and as a result, pH of the artificial urine was greatly increased to about 8 or more.

On the other hand, Comparative Example 4, in which the antimicrobial monomer was simply mixed, showed CRC and antimicrobial property at equivalent levels to those of Examples, but a large amount of the antimicrobial monomer was leaked out. In contrast, the superabsorbent polymers of Examples 1 to 3 showed no leakage or very small leakage of antimicrobial monomer, and thus it was confirmed that the superabsorbent polymers of Examples may continue to exhibit excellent antimicrobial properties without leakage of the antimicrobial monomer even over time.

With regard to leakage of the antimicrobial monomer, no polymerizable antimicrobial monomer was detected in the superabsorbent polymer using GA or MGU, in which the guanidine moiety was bound by covalent bonds, whereas a small amount of guanidine monomer was detected in the superabsorbent polymer using GAS or GMA formed by ionic bonds contained. It is assumed that this is caused by slight dissociation of ionic bonds during the process of evaluating the leakage of monomers. In contrast, in Comparative Example 4, in which guanidine acrylate was simply mixed, a large amount of antimicrobial monomer was detected, and it was confirmed that when the superabsorbent polymer was prepared by comprising the antimicrobial monomer without copolymerizing, the leakage of the antimicrobial monomer to the outside occurred seriously.

Experimental Example 2

Deodorant property was evaluated for the superabsorbent polymers prepared in Examples and Comparative Examples by the following methods.

In detail, each of the superabsorbent polymers prepared in Examples and Comparative Examples was injected into 50 ml of artificial urine, in which 10,000 CFU/ml of *Proteus Mirabilis* (ATCC 29906) was inoculated, at a concentration of 0.4 mg/ml per 1 ml of solvent, and incubated in a shaking incubator (Vison Tech, VS-37SIF) at 35° C. for 12 hours. After connecting an ammonia detector tube (Gastec, ammonia 3M) and a suitable pump (Gastec, GV-100) to the container, in which the culture was completed, 50 ml was extracted using an injection needle. The color of the detector tube was changed by ammonia, and the scale was checked and compared. The composition of artificial urine used at this time was prepared using a method suggested in *J Wound Ostomy Continence Nurs.* 2017; 44(1) 78-83. The results are shown in Table 4 below.

TABLE 4

| | Kind of antimicrobial monomer | Content of antimicrobial monomer (parts by weight[1]) | Concentration of ammonia (ppm) |
|---|---|---|---|
| Example 1 | GA | 1.0 | 130 |
| Example 2 | GA | 2.0 | 25 |
| Example 3 | GAS | 2.0 | 62 |
| Comparative Example 1 | — | — | 385 |
| Comparative Example 2 | GMA | 2.0 | 310 |
| Comparative Example 3 | MGU | 2.0 | 285 |
| Comparative Example 4 (simple mixing) | GA | 2.0 | 30 |

In Table, parts by weight[1] is a relative weight ratio based on 100 parts by weight of acrylic acid monomer.

In Examples and Comparative Examples, the ammonia generated in the pure bacterial culture solution without the antimicrobial monomer exceeded the measurable range of 500 ppm in the detector tube. When the superabsorbent polymers using GA or GAS of Examples 1 to 3, and Comparative Example 4 were used, the ammonia generation was greatly reduced, as compared with Comparative Examples 2 and 3 using GMA or MGU. In addition, when compared on the basis of the equivalent amount, GA showed a better ammonia reduction effect than GAS.

The invention claimed is:
1. A superabsorbent polymer comprising:
a base polymer powder comprising a crosslinked polymer of water-soluble ethylene-based unsaturated monomers having acidic groups of which at least a part are neutralized, and a polymerizable antimicrobial monomer; and
a surface crosslinked layer formed on the base polymer powder, in which the crosslinked polymer is additionally crosslinked by a surface crosslinking agent;
wherein the polymerizable antimicrobial monomer comprises one or more of guanidine acrylate and salts thereof.

2. The superabsorbent polymer of claim 1, wherein the guanidine acrylate is a compound represented by the following Chemical Formula 1:

[Chemical Formula 1]

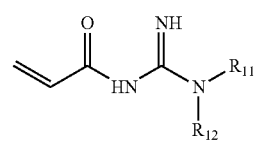

in Chemical Formula 1,
$R_{11}$ and $R_{12}$ are each independently hydrogen or an alkyl group having 1 to 20 carbon atoms.

3. The superabsorbent polymer of claim 1, wherein the salt of guanidine acrylate is a compound represented by the following Chemical Formula 2:

[Chemical Formula 2]

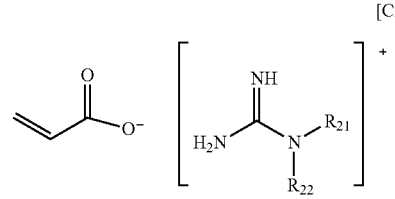

in Chemical Formula 2,
$R_{21}$ and $R_{22}$ are each independently hydrogen or an alkyl group having 1 to 20 carbon atoms.

4. The superabsorbent polymer of claim 1, wherein the polymerizable antimicrobial monomer comprises one or more of compounds represented by the following Chemical Formulae:

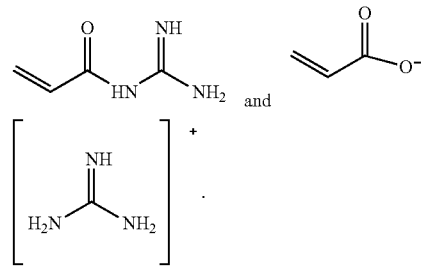

5. The superabsorbent polymer of claim 1, wherein the superabsorbent polymer has a 30-min centrifuge retention capacity of 29 g/g to 50 g/g for a physiological saline solution (0.9 wt % aqueous sodium chloride solution), as measured in accordance with EDANA method WSP 241.3, and exhibits antimicrobial property against Gram-negative bacteria.

6. The superabsorbent polymer of claim 5, wherein the Gram-negative bacteria is *Proteus mirabilis* or *E. coli*.

7. A method of preparing the superabsorbent polymer of claim 1, the method comprising:

carrying out a crosslinking polymerization of water-soluble ethylene-based unsaturated monomers having acidic groups of which at least a part are neutralized, and a polymerizable antimicrobial monomer, in the presence of an internal crosslinking agent, to form a hydrogel polymer;

drying, pulverizing, and classifying the hydrogel polymer to form a base polymer powder; and carrying out additional crosslinking of the base polymer powder by heat treatment in the presence of a surface crosslinking agent, wherein the polymerizable antimicrobial monomer comprises one or more of guanidine acrylate and salts thereof.

8. The method of claim 7, wherein the polymerizable antimicrobial monomer comprises one or more of compounds represented by the following Chemical Formulae:

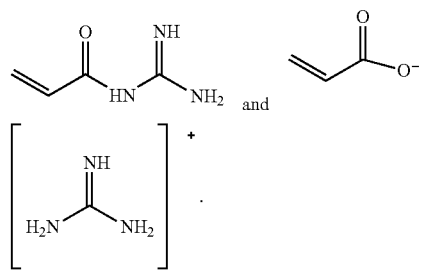

9. The method of claim 7, wherein the polymerizable antimicrobial monomer is used in an amount of 0.01 part by weight to 10 parts by weight with respect to 100 parts by weight of the water-soluble ethylene-based unsaturated monomers.

10. The method of claim 7, wherein the crosslinking polymerization is carried out by photopolymerization.

11. A hygiene product comprising the superabsorbent polymer of claim 1, wherein the hygiene product is a diaper or sanitary pad.

* * * * *